United States Patent
Magaraggia et al.

(10) Patent No.: US 11,717,358 B2
(45) Date of Patent: Aug. 8, 2023

(54) MEDICAL ENGINEERING ROBOT, MEDICAL SYSTEM, METHOD FOR OPERATION THEREOF, COMPUTER PROGRAM, AND STORAGE MEDIUM

(71) Applicant: Siemens Healthcare GmbH, Erlangen (DE)

(72) Inventors: Jessica Magaraggia, Erlangen (DE); Gerhard Kleinszig, Forchheim (DE); Maddalena Strumia, Forchheim (DE); Alois Regensburger, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 778 days.

(21) Appl. No.: 16/745,708

(22) Filed: Jan. 17, 2020

(65) Prior Publication Data
US 2020/0229879 A1   Jul. 23, 2020

(30) Foreign Application Priority Data
Jan. 23, 2019   (DE) .......................... 102019200803.8

(51) Int. Cl.
*A61B 34/30* (2016.01)
*A61B 1/00* (2006.01)
(Continued)

(52) U.S. Cl.
CPC .......... *A61B 34/30* (2016.02); *A61B 1/00149* (2013.01); *A61B 2034/301* (2016.02);
(Continued)

(58) Field of Classification Search
CPC ..... A61B 1/00149; A61B 34/30; A61B 34/32; A61B 34/70; A61B 2034/301–303; A61M 25/108; A61M 25/0116
See application file for complete search history.

(56) References Cited

U.S. PATENT DOCUMENTS

2009/0299132 A1 * 12/2009 Takahashi .............. A61B 34/30
                                                                600/37
2010/0262162 A1 * 10/2010 Omori .................... A61B 34/70
                                                               606/130

(Continued)

FOREIGN PATENT DOCUMENTS

EP            3384846 A1   10/2018
WO   WO2017214243 A1   12/2017

OTHER PUBLICATIONS

Fischer, Peter, et al. "Surrogate-driven estimation of respiratory motion and layers in x-ray fluoroscopy." International Conference on Medical Image Computing and Computer-Assisted Intervention. Springer, Cham, 2015. 99. 282-289.

(Continued)

*Primary Examiner* — John P Leubecker
(74) *Attorney, Agent, or Firm* — Lempia Summerfield Katz LLC

(57) ABSTRACT

The disclosure relates to a medical engineering robot, a medical system, a method for operation thereof, a corresponding computer program, and a corresponding computer-readable storage medium. By controlling a pose of an instrument arm of the robot relative to a respective examination object to be treated or to be examined by the robot, the disclosure makes provision for automatically bringing the instrument arm into contact with the examination object and through this for setting a predetermined pose of the examination object.

20 Claims, 2 Drawing Sheets

(51) Int. Cl.
*A61B 90/00* (2016.01)
*A61M 25/01* (2006.01)

(52) U.S. Cl.
CPC .. *A61B 2090/3764* (2016.02); *A61M 25/0108* (2013.01); *A61M 25/0116* (2013.01)

(56) References Cited

U.S. PATENT DOCUMENTS

| | | | |
|---|---|---|---|
| 2011/0060345 A1* | 3/2011 | Lee | A61B 34/30 606/130 |
| 2011/0245844 A1* | 10/2011 | Jinno | A61B 34/30 606/130 |
| 2013/0303893 A1* | 11/2013 | Duindam | A61B 5/066 600/424 |
| 2014/0142422 A1* | 5/2014 | Manzke | A61B 5/4839 600/424 |
| 2014/0163736 A1* | 6/2014 | Azizian | A61B 6/102 700/259 |
| 2015/0112126 A1* | 4/2015 | Popovic | A61F 2/062 600/102 |
| 2015/0190204 A1* | 7/2015 | Popovi | A61B 6/027 600/424 |
| 2018/0132839 A1* | 5/2018 | Friedrich | A61B 34/76 |
| 2018/0193102 A1* | 7/2018 | Inoue | A61B 1/05 |
| 2018/0221098 A1* | 8/2018 | Forsyth | A61B 34/74 |
| 2018/0233222 A1* | 8/2018 | Daley | G16H 50/50 |
| 2019/0201139 A1* | 7/2019 | Shelton, IV | A61B 34/76 |
| 2019/0328599 A1* | 10/2019 | Mahoney | A61G 13/1245 |
| 2020/0315721 A1* | 10/2020 | Rabindran | A61B 34/35 |
| 2021/0030494 A1* | 2/2021 | Panescu | A61B 34/32 |

OTHER PUBLICATIONS

German Office Action for German Application No. 10 2019 200 803.8 dated Sep. 16, 2019.

* cited by examiner

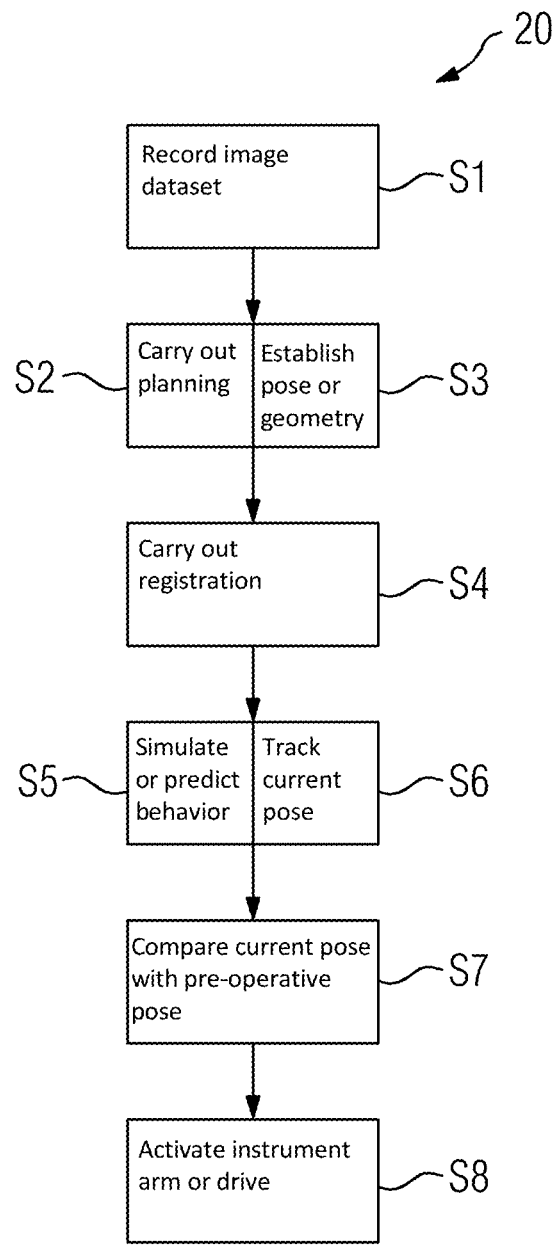

MEDICAL ENGINEERING ROBOT, MEDICAL SYSTEM, METHOD FOR OPERATION THEREOF, COMPUTER PROGRAM, AND STORAGE MEDIUM

The present patent document claims the benefit of German Patent Application No. 10 2019 200 803.8, filed Jan. 23, 2019, which is hereby incorporated by reference.

TECHNICAL FIELD

The disclosure relates to a medical engineering robot and to a medical system, which includes such a medical engineering robot, as well as to a method for operating such a medical engineering robot or such a medical system respectively. The disclosure further relates to a corresponding computer program, which encodes or represents the method, as well as to a computer-readable storage medium on which a corresponding computer program is stored. Medical engineering is an exemplary field of application of the present disclosure. This is, however, not intended to exclude the present disclosure from being able to be used to good effect in other technical fields or areas of application.

BACKGROUND

Medical applications or interventions, (e.g., bronchoscopes or endovascular or gastrointestinal endoscopic procedures or interventions), may be carried out with the support of devices, robots, and data processing methods. In particular, there is nowadays widespread use of computer-supported planning of procedures or interventions, in the course of which, for example, based on an image dataset of a respective examination object (e.g., a patient) recorded pre-operatively or pre-interventionally or intra-operatively, a target region for the respective intervention as well as an instrument path is planned and defined. This may theoretically make an especially reliable, low-stress, and precise execution of the respective intervention possible.

However, the problem, which arises, is that movements or deformations of the examination object may occur during the respective intervention, which lead to the prior planning not being able to be readily followed. For example, a position or pose of the respective target region, (e.g., a lesion), and/or the geometry of an organ or vessel, may change during the intervention in relation to a pre-interventional state such that, based on the pre-interventional or intra-interventional planning, the intended instrument path cannot be readily followed or a number of approaches or attempts are necessary to actually find the target region, or the intervention even has to be aborted. These kinds of movements or deformations of the examination object in or during the respective intervention may have various causes, for example, a breathing movement or a tissue deformation as a result of using or moving devices or other technical aids, such as clamps, supports or the like, for example. Effectively this may make the respective image dataset recorded pre-interventionally highly imprecise in relation to a situation or geometry of the examination object that actually exists during the intervention.

For a correct, reliable and low-stress execution of the respective intervention however, a reliable and precisely supported navigation or guidance along a planned instrument path to the respective target region in each case would be desirable, so that, during the intervention itself, a dynamic and possibly demanding adaptation or replacing of the intervention and/or one that is stressful for the examination object, and also for the respective medical personnel as well, is not necessary.

SUMMARY AND DESCRIPTION

The object of the present disclosure is to make possible a navigation of an instrument in a way that is reliable and is non-stressful for the respective examination object.

The scope of the present disclosure is defined solely by the appended claims and is not affected to any degree by the statements within this summary. The present embodiments may obviate one or more of the drawbacks or limitations in the related art.

A medical engineering robot, e.g., a medical robot for robotically supported surgery, for example, has a movable instrument arm, a drive for moving the instrument arm, and a control device connected to the drive for automatically controlling a pose of the instrument arm. The control device is configured, by controlling the pose of the instrument arm relative to a respective examination object to be treated or to be examined by the robot, to bring the instrument arm automatically into contact with the examination object and thereby to set a predetermined pose, (e.g., a position, setting, and/or geometry), of the examination object, that is to bring it about. In other words, the robot is designed and configured actively to create or to bring about a desired or intended pose, geometry, or change in shape of the examination object through corresponding control.

The examination object may be a patient or a part area of a patient for example. Further part areas, regions or locations may be defined as part of the examination object, for example, a target region for an intervention. Such a target region (also referred to as a Region of Interest, RoI) may be a diseased or injured point in the tissue, for example. Bringing the robot or the instrument arm into contact with the examination object may in this case mean or include establishing mechanical contact between the robot and the examination object on or in the area of the target region and/or in other parts or areas of the examination object. In the latter case, this may still possibly involve a location of the target region and/or a way or path to the target region, as well as in particular its ability to be reached, being influenced.

The movable instrument arm of the robot may have or include a number of segments connected to one another by an articulated joint in each case. Accordingly, the robot may be a lightweight robot or the like having, in certain examples, at least six degrees of freedom. Likewise, the instrument arm may be entirely or partly flexible, in particular, bendable dynamically and under continuous control, (e.g., a snake robot), by a number of actuators, for example. The actuators may be arranged along the instrument arm and/or be connected by cables, wires, or pulls to one or more part areas of the instrument arm in each case, in order to move the corresponding part area or part areas, in particular relative to other part areas of the instrument arm in each case, to control or to set the respective pose of the instrument arm. Likewise, for example, an electrical control of the pose of the instrument arm may be possible by a tension-dependent geometry or stiffness of the instrument arm.

The drive of the robot may include one or more electric motors, hydraulic and/or pneumatic actuators or devices or the like, for example.

The control device may include a data processing facility, (e.g., a computer or a microcontroller or the like), as well as a data memory connected thereto with a corresponding operating program or control program for the robot. To control or set the pose of the instrument arm the control device may generate corresponding control signals and transfer them to the drive of the robot, for example. The control device may further have at least one data interface for acquisition of data, which may be provided by other facilities or devices, for example. The control device may take account of data received via this data interface in the control of the instrument arm, e.g., in the control or setting of the pose of the instrument arm. Such data may be or include specifications about the desired or intended predetermined pose of the examination object, about a current pose or geometry of the examination object, registration or coordination or synchronization data for registering or coordinating a coordinate system used by the robot with a coordinate system used by an imaging device provided or used for imaging the examination object, and/or more besides, for example.

The robot may have a position monitoring system or position determination system, by which the robot may determine or establish its own pose, for example, in the robot's own internal coordinate system. The pose of the robot determined in this way, in particular of the instrument arm or of the individual segments, articulated joints or part areas of the instrument arm, is also referred to as the absolute pose or absolute position of the robot or of the instrument arm respectively. A conventional robot kinematic system may be employed here, for example. The position monitoring or position determination system of the robot may thus include a kinematic model of the robot, in particular, a simulation device for simulating or modelling a movement or pose or a change in pose of the robot with reference to the kinematic model and/or sensor data that characterize the movement and/or pose of the robot. The position monitoring system may include sensors arranged along the instrument arm, for example, at least one force, moment, bending, acceleration and/or angle sensor, an inertial measurement unit, (IMU), a fiber Bragg grating and/or the like, which may transfer their respective sensor data to the control device. Not only may the movement or pose of the robot be determined and tracked by these sensors or the corresponding sensor data, but it may likewise be established whether and if necessary which parts or segments of the robot, in particular, of the instrument arm, may move freely or are in mechanical contact with their surroundings or with a foreign object, here in particular the examination object.

In addition, or as an alternative, a tracking system for determining and tracking the current pose of the instrument arm in each case may be provided. This may be an external electromagnetic tracking system, for example. Likewise, the instrument arm may be tracked entirely or in part during the examination or treatment of the examination object in an image-based manner, e.g., with reference to image data provided by an external camera or an image device used for imaging the examination object. Corresponding position data, which specifies the pose of the instrument arm or of a part of the instrument arm, may then be transferred via the data interface to the control device, for example, which may then be configured to take into account, e.g., to evaluate or to process, this position data for controlling the pose of the instrument arm.

The control of the pose of the instrument arm may mean or include changing the pose, e.g., a translational and/or rotational movement of at least a part area of the instrument arm. The control of the pose of the instrument arm may likewise be able to include or to mean holding the instrument arm or a part of the instrument arm in a specific pose, in particular, against an external force. The control device may thus be configured, for example, within the framework of controlling the pose of the instrument arm, for stiffening the arm or, for example, at least one articulated joint of the instrument arm and/or for compensating for an external force acting on the instrument arm by the drive, in order to hold it in a respective pose. Such an external force may be exerted by the examination object coming into contact with the instrument arm. The control of the pose of the instrument arm relative to the examination object may thus take account of a movement of the instrument arm towards the examination object and also of a movement of the examination object towards the instrument arm.

The setting of the pose of the examination object via the mechanical contact between the examination object and the instrument arm may thus mean that the examination object may be displaced or be changed in shape or deformed by the instrument arm, in order to generate the predetermined pose or geometry of the examination object. Likewise, by corresponding stiffening or holding the instrument arm in a specific pose, for example, a movement of the examination object may be prevented or be limited or restricted. In this sense, the setting of the pose of the examination object may thus mean or include preventing a deviation from this pose.

A concept of the disclosure thus lies in the knowledge that the movable and actively controllable instrument arm of the robot, which in the past could contribute in a disadvantageous manner to displacements or deformations of the examination object, may be used, through appropriate control of the pose or movement of the instrument arm, to counteract these disadvantageous displacements or changes in shape of the examination object. For example, a given pre-operative or pre-interventional pose, or geometry of the examination object acquired by an imaging process may be predetermined as the predetermined pose, e.g., as the intended reference. The instrument arm may then be controlled, e.g., moved, during the respective examination or treatment of the examination object so that, even during the examination or treatment, the geometry or pose of the examination object given pre-interventionally will at least essentially be maintained or retained or will be established.

In addition, or as an alternative, for example, by a movement or displacement or deformation of the examination object by the instrument arm, e.g., such as by the instrument arm being pressed or moved against the examination object, the predetermined pose of the examination object may be set, for example, in order maybe to make it possible for the instrument arm or for an instrument held or guided by the instrument arm or a separate instrument to reach a respective target region better or more easily. For example, a force may be exerted by the instrument arm on a part area of a patient, such as on an organ, in order, for example, to bring about or to set a specific, (e.g., straightened), course of a vessel within this organ or the like. Thus, in an advantageous embodiment, the robot may be configured to assess the instrument's ability to reach a predetermined target region on the basis of at least one predetermined geometrical criterion and to control the instrument arm as a function of the reachability against the examination object, in order to improve the reachability. The target region may be a lesion, a tumor, a narrowing, or constriction of a vessel or the like. The target region may be defined, e.g., predetermined, on the basis of a pre-interventional dataset, for example. The robot may be configured to acquire this dataset and/or a specified position for the target region as input data. Likewise, the robot may be configured intra-interventionally to acquire a current geometry of the examination object, in particular a position or pose of the target region, or corresponding data and to assess its reachability on the basis of this data. The geometrical criterion may be or include a size of a free space in front of or next to the target region, a distance between the target region and neighboring tissue, a curvature of a vessel or hollow organ in a section leading to the target region, an angle or a position of a surface of the target region relative to surrounding tissue and/or relative to a hollow volume or the like intended or planned as the instrument path and/or more besides. The robot may thus actively move the instrument arm against the wall of a vessel or tissue, which is connected to a vessel intended as the instrument path, and thereby alter a bending, a curvature or a course of the vessel such that the geometrical criterion, e.g., at least a predetermined reachability criterion, is fulfilled or at least a measure of assessment is enlarged or improved.

A further example for an application to be used advantageously is Endoscopic Retrograde Cholangio Pancreatography (ERCP). In such a procedure, an active deformation of the respective patient, (e.g., a simplified cannulation of the papilla), may be made possible by the robot through appropriate control of the instrument arm.

The robot, (e.g., the control device), may be configured to predict, to model, or to simulate a behavior of the examination object under mechanical contact with the instrument arm, for example, on the basis of or by a biomechanical model of at least a part area of the examination object. In this way, the predetermined pose of the examination object may be set precisely and reliably by appropriate control of the pose of the instrument arm in accordance with a previous modelling or simulation or prediction. This will be described in greater detail further on in this document.

The present disclosure may advantageously make enhanced consistency between a pre-interventional and an intra-interventional situation, in particular geometry, of the respective examination object possible and thereby contribute to a simplified, more precise and especially reliable execution of the respective intervention or treatment or examination. Because it may thus be achieved by the present disclosure that an intra-interventional situation or geometry at least essentially corresponds to the respective pre-interventional situation or geometry and thereby, the pre-interventionally planned instrument path may be followed intra-interventionally, in order to find the respective target region reliably, an intra-interventional radiation load on the examination object for monitoring the current pose of the examination object or a dose of contrast medium necessary for this may be reduced by comparison with conventional navigation methods, for example. This advantageously enables a load on the examination object to be reduced. Likewise, the present disclosure enables reaching a respective target region to be improved or simplified for a medical instrument, whereby the target region is advantageously made able to be reached more reliably, more quickly, and/or with a greater diversity of instruments, through which not only may the chances for success of an examination or treatment be improved, but if necessary the time necessary to do this may also be reduced, which may advantageously be accompanied by reduced stress both for the examination object and also for respective medical personnel. Advantageously, the present disclosure uses existing hardware for this, so that no additional outlay in components or devices is necessary and for example no clamps or supports or the like to define part areas of the examination object have to be introduced into the object. The stress for the examination object may also be reduced by this and the respective intervention carried out more efficiently.

In a further advantageous embodiment, the robot is configured, through active control of the instrument arm relative to the examination object, to counteract a deformation of the examination object, in particular to balance out or compensate for the deformation at least in some areas. This advantageously enables, at least in some areas, such as in the area of a predetermined target region of the examination object, a geometry that is at least essentially independent of a movement or deformation of the examination object and remains essentially the same, to be reached or maintained. In this case account may be taken where necessary for example, of an increased scope of movement in other areas of the examination object by which a respective intervention or examination will not be influenced.

In further advantageous embodiments, the robot has a medical instrument, in particular a catheter and/or an endoscope. In this case the instrument arm is embodied as this medical instrument or the medical instrument is fastened or held on the instrument arm, for example on an end-side robot flange of the instrument arm. In addition, or as an alternative, in this case at least one part of the medical instrument is embodied as visible to x-rays. This means that at least the corresponding part of the instrument that is visible to x-rays is able to be imaged by conventional x-ray devices, is, e.g., opaque or non-transparent for x-ray radiation. The robot may thus be embodied here for controlling, guiding, or handling the medical instrument. In conjunction with the embodiment of the medical instrument visible to x-rays, this makes possible an especially advantageous and flexible usability and applicability of the robot for medical applications or interventions, for example surgical interventions, interventional diagnostics, as part of a biopsy for example, and/or further interventional therapies, such as an ablation. In particular, in this way, in an especially simple manner, an incorporation of the robot into interventional procedures or workflows is made possible, which makes possible intra-interventionally an x-ray-based imaging modality provided for imaging of the examination object. For example, a registration between the coordinate systems of the robot and of the imaging modality as well as an x-ray-image-based tracking or supervision of the pose of the instrument is made possible in an especially simple way. This in its turn makes possible an additional safeguarding of the robot control for example, for example, a recognition and balancing out of drift not detected by the robot itself or by its position monitoring system. One field of application of the robot embodied in this way may thus lie, for example, in fluoroscopy or fluoroscopically supported interventions respectively.

A monitoring, e.g., a supervision, of a current deformation status of the examination object, e.g., of its current deformation or geometry, and/or of the robot, may however likewise be done as an addition or exclusively on the basis of a sensor system of the robot arranged internally and/or on the robot, in particular on the instrument arm. This then advantageously if necessary, enables visibility, at least a continuous visibility, of the robot to be dispensed with in imaging. Tracking based on the sensor system of the robot, e.g., supervision of the tracking, of the geometry of the examination object and/or of the robot may however, as described, be supplemented or supported by further methods, for example, an electromagnetic and/or image-based tracking. This means that the present disclosure is advantageously very flexible and able to be used with diverse equipment available in an individual case.

In a further advantageous embodiment, the robot is configured to acquire breathing data, which specifies or characterizes a respective current breathing phase, e.g., a breathing cycle or a breathing movement, of the examination object. The control device is configured in this case to control the pose of the instrument arm as a function of the breathing data. The examination object may thus in particular be a patient here, wherein their breathing leads to a movement and/or deformation. The breathing movement or the deformation of the examination object accompanying the movement, e.g., of the patient or of a part area of the patient, may in such cases not be predicted in each case on the basis of pre-interventional data or be subject to a controlled check in another way. For example, not every patient may breathe sufficiently evenly, and an artificially controlled breathing is not practicable in any case.

The control device may be configured here, in a specific breathing phase or at a specific point or during a specific section of the breathing cycle of the respective patient for example, to stiffen the instrument arm or to move it or control it into a specific pose, in order, for example, to prevent or to limit the breathing movement or a movement of a part area of the patient brought about by the movement. Likewise, an active deformation of the instrument arm as a function of the breathing phase or the breathing cycle is possible, in order to compensate for a deformation of the examination object, (at least in a part area of the examination object such as in the area of the predetermined target region), otherwise accompanying the breathing. In this way, the predetermined pose of the examination object, (e.g., a course of a vessel or a relative or absolute position or pose of a defined target region), may be safeguarded or set, e.g., also for irregular or uncontrolled or unpredictable breathing. Thus, for example, it may be prevented that the bending radius of a vessel, in which an instrument is guided during the intervention or, for example, a stent or the like is to be placed, falls below a predetermined minimum value as a result of the breathing movement for example or the respective target region, (e.g., a lesion or a tumor or a vessel branch or the like), is hidden by another area of tissue as a result of the breathing movement for example or more besides. In this case, during the other breathing phases or during the other sections of the breathing cycle, the robot or an instrument guided or held by the robot, may be guided, moved or inserted flexibly, as per requirements. This means that the present disclosure may advantageously especially flexibly and reliably make possible or support, without additional instruments or aids, the carrying out of interventions and in this way contribute to the wellbeing of the patient. The acquisition of breathing data in this case may mean receiving the breathing data, for example, via the data interface. In such cases, the breathing data may thus be provided by an external device or an external data source, for example, a chest belt or the like. Likewise, the robot itself may have a facility for measuring or determining the breathing phase or the breathing cycle respectively, e.g., may establish the breathing data by itself.

In an advantageous development, the control device is configured, in a predetermined breathing phase in each case, in which the examination object, as a result of their breathing movement, comes into contact with the instrument arm, to stiffen the instrument arm in a predetermined position, for example, in its current position or pose in each case, and thereby to limit the breathing movement of the examination object. The stiffening of the instrument arm thus means that, through corresponding control of the instrument arm or of the drive respectively, a bending or deformation or shifting of the instrument arm through the contact with the examination object, e.g., through a force exerted by the examination object on the instrument arm, is prevented or made more difficult. In particular, the stiffening enables the instrument arm to thus be fixed or held in a fixed position in its position or pose relative to the examination object. To stiffen the instrument arm at least one articulated joint of the instrument arm may be latched or locked, or a brake may be activated for example. In addition, or as an alternative, the instrument arm may be stiffened by the drive by automatic application of a force. Depending on embodiment or material composition of the instrument arm, an electrical voltage and/or a pneumatic or hydraulic pressure may likewise automatically be adapted for example, in order to bring about the stiffening of the instrument arm.

As already explained, depending on the breathing phase or the breathing movement, for example, a movement going beyond a predetermined limit or threshold value, displacement, or deformation of the examination object may be avoided by the stiffening of the instrument arm and thereby an adverse effect on the carrying out of the respective intervention may be avoided or prevented. The fact that the instrument arm is only stiffened in the predetermined breathing phase however, e.g., not during the entire breathing cycle, means that there is still the opportunity of moving or of controlling the instrument arm flexibly outside the predetermined breathing phase, so that thus even complex interventions may continue to be carried out or remain able to be carried out.

In a further advantageous embodiment, the control device contains or includes a predetermined biomechanical model of at least a part of the examination object. The biomechanical model may be stored in the data memory, for example. The control device is configured here, by simulating a behavior of at least the part of the examination object under mechanical contact with the instrument arm which is modeled or described or characterized by the predetermined biomechanical model, automatically to determine by the biomechanical model a pose of the instrument arm needed for setting the predetermined pose of the examination object and/or a force to be exerted by the instrument arm on the examination object for setting the predetermined pose of the examination object. The control device is further configured to generate corresponding control signals for the drive, wherein these control signals thus bring about the setting of the specific pose needed and/or an application of the specific force to be exerted.

The biomechanical model may model, characterize, or describe, at least for the part of the examination object, (e.g., a mechanical and/or hydrodynamic behavior), an elasticity or deformability, a compression mobility or compressibility, a limitation or restriction of movements or deformations of the part of the examination object, for example, as a result of its internal structure and/or because of surrounding tissue or corresponding connections and/or more besides. The biomechanical model may be or include a model of a part area of the patient, of a tissue structure, of an organ, or the like. The biomechanical model may be realized in various ways, for example, based on an FEM (FEM: Finite Elements Method/Finite Elements Model), as a computer graphics model, as a stiffness model and/or more besides.

Boundary conditions or assumptions may be predetermined for the biomechanical model in line with requirements, for example, depending on available data about the examination object and/or depending on available computing power. The starting point may be a change in shape or deformation with minimum energy requirement or a maximum stiffness of the examination object, which allows a respective movement or deformation (e.g., as-rigid-as-possible model). This may advantageously reduce a computational outlay for simulating the behavior of the examination object.

The biomechanical model may be created or generated from a pre-interventionally recorded 3D or 4D image dataset or measurement dataset of the examination object for example. In concrete terms the biomechanical model may be created from a CT or MRT or ultrasound dataset, for example.

Especially advantageously the biomechanical model may be continuously updated during the intervention, e.g., during an operation or deployment of the robot, automatically by the control device on the basis of data available in each case, for example, image or position data and/or sensor data of a sensor system of the robot. This may advantageously make possible an especially precise and reliable simulation of the behavior of the examination object during the current intervention in each case and/or for future interventions.

The model-based simulation of the behavior of the examination object enables the predetermined pose of the examination object advantageously to be set especially efficiently, e.g., especially rapidly or with minimal movements of the instrument arm or with minimal force for instance, and especially reliably. To this end various poses, various forces, forces exerted at various points of the examination object and/or more besides to be simulated one after another or in parallel to one another for example. A pose and/or force may then be selected automatically by the control device, which makes possible a minimal adverse effect on the examination object or on a respective workflow of the intervention. In this way, having to bring the instrument arm into contact with the examination object multiple times in multiple ways and/or with different forces may thus advantageously be avoided for example, until the predetermined pose of the examination object is reached or set, which enables time to be saved and stress for the examination object as well as a risk of injury to the examination object to be minimized.

In a further advantageous embodiment, the robot has a stress, load, and/or stiffness sensor system arranged on the instrument arm for determining a mechanical property of a part of the examination object in mechanical contact with the instrument arm in each case. In this case, the control device is configured automatically to determine the pose of the instrument arm needed for setting the predetermined pose of the examination object and/or a force to be exerted for this purpose by the instrument arm on the examination object as a function of the mechanical property determined. Its deformation or deformability, elasticity, movability, or displaceability and/or more may be determined as the mechanical property of the examination object, for example. In particular, the mechanical property may be, describe, or characterize a respective current pose or geometry of the examination object. In this embodiment, the biomechanical model of the examination object for simulating its behavior may advantageously be dispensed with. The stress, load, and/or stiffness sensor system may include one or more force, moment, and/or bending sensors, for example. The control device may then automatically deduce from the changes of respective sensor or measured values of the sensor system for a mechanical contact between the instrument arm and the examination object, the mechanical property, the pose, and/or the geometry. This advantageously enables a separate supervision or determination of the corresponding mechanical property to be saved or reduced.

A further aspect of the present disclosure is a medical system, which includes a medical imaging device for imaging an examination object, (e.g., a patient or a part area of a patient) and has a medical engineering robot connected to this imaging device. In this case, the control device of the robot is configured to control the pose of the instrument arm of the robot automatically as a function of data provided by the medical imaging device, (e.g., image or position data), which specifies or describes a current pose or geometry of at least a part area of the examination object in each case, and thereby automatically to set the predetermined pose of the examination object.

As a basis for the corresponding control or regulation of the instrument arm or of the drive of the robot respectively by the control device, the control device may automatically, (e.g., continuously), determine a difference or discrepancy between the predetermined pose (e.g., based on a pre-operative or pre-interventional image dataset) and a current pose in each case, (e.g., a live pose), of the examination object and compensate for the difference determined by appropriate control of the instrument arm.

The robot and the imaging device of the medical system may be arranged in a predetermined and/or in a spatial positional relationship tracked during the operation of the system relative to one another, for example, use the same coordinate system, through which the robot may be controlled directly based on the data provided by the medical imaging device. Likewise, the medical system may be embodied and configured for an automatic registration between coordinate systems of the robot and of the imaging device. Thus, for example, at each deployment position or before each use of the medical system, a corresponding registration of the coordinate systems is carried out, in order to make possible a control of the robot that is coordinated as simply and as reliably as possible as a function of the data provided by the medical imaging device.

For acquiring and tracking the pose of the robot or of the instrument arm respectively, the medical system may have a tracking facility arranged in a predetermined, (e.g., constant or fixed), spatial positional relationship to the imaging device, (e.g., a tracking system). This tracking system may have one or more cameras, (e.g., a stereo camera), and/or facilities for an electromagnetic tracking. Corresponding markers able to be acquired by the tracking system may be arranged on the robot, in particular, on the instrument arm. In this way, the registration between the coordinate systems of the robot and the imaging device may then be carried out especially simply and reliably with conventionally known methods.

A further aspect of the present disclosure is a method for operating a medical engineering robot and/or a medical system. The method includes determining, (for example, calculating, measuring, or acquiring), a default or input of an intended pose of at least a part of the respective examination object.

This intended pose may be the predetermined pose of the examination object mentioned in conjunction with the medical engineering robot and/or the medical system. The method further includes automatically determining a pose of the instrument arm of the robot relative to the examination object needed for setting the intended pose of the examination object and/or a force to be exerted to do this by the instrument arm on the examination object, e.g., to set the intended pose of the examination object. The method further includes a corresponding automatic control or setting of the instrument arm in accordance with the determined pose and/or force to be exerted by the control device for setting the predetermined intended pose of the examination object.

In other words, the method thus includes measures, processes, or execution sequences described in conjunction with the medical engineering robot and/or in conjunction with the medical system. Further processes, measures or execution sequences mentioned in this context may be provided as, if necessary optional, further method acts of the method.

It should be pointed out at this point that any surgical acts or measures mentioned or indicated to illustrate the present disclosure are explicitly not part of the disclosure claimed here, in particular not part of the method. In other words, the method does not include a surgical act. This does not conflict with the ability to execute or use the present disclosure, however. For example, the medical engineering robot may be brought into mechanical contact with the examination object from outside, e.g., without surgical intervention, in order to set the predetermined pose of the examination object. The fact that the method may be usefully applied in parallel to a surgical act, the robot or the medical system respectively may thus be usefully employed or operated during a surgical intervention for example, merely illustrates the advantageous applicability of the present disclosure, but does not represent any claim to the corresponding surgical acts or measures. Finally, the method relates to a control of the medical engineering robot or of the medical system respectively and is thereby independent of any possible surgical interventions or measures.

In an advantageous development, a pre-interventional pose of the examination object is predetermined in accordance with a respective pre-interventionally created image dataset of the examination object intended for intervention planning and accordingly predetermined as the intended pose of the examination object. This advantageously makes possible an especially precise and reliable intervention planning as well as an advantageously especially simple ability to execute the respective intervention as planned.

A further aspect of the present disclosure is a computer program or computer program product for a medical engineering robot and/or for a medical system. The computer program may thus be a control program or operating program or operating system for or robot or the medical system respectively. The computer program or computer program product includes commands or control instructions, which, when the computer program is executed by a computer or a data processing facility of the medical engineering robot or of the medical system respectively, causes these to carry out the method acts of the method. The computer program thus encodes or represents the method.

A further aspect of the present disclosure is a computer-readable storage medium, e.g., a data medium or data memory on which a computer program or computer program product is stored.

The medical engineering robot or the medical system may be embodied to carry out, in particular, automatically or semi-automatically, the method. To this end, the medical engineering robot or the medical system may have a computer-readable storage medium in each case. For execution of the computer program stored thereon, e.g., program code, the medical engineering robot or the medical system may have a respective data processing device, in particular, a processor device connected to the respective computer-readable storage medium for executing the computer program stored thereon, for example a microprocessor, microchip, or microcontroller.

A further aspect of the present disclosure is a data carrier signal, which a computer program transmits.

The characteristics and developments of the medical engineering robot, of the medical system, of the method, of the computer program and of the computer-readable storage medium specified above and below are each able to be mutually transmitted between these aspects of the present disclosure. Such developments of the aspects of the disclosure, which have embodiments, which, to avoid unnecessary redundancy are not described explicitly here in the respective combination or not described separately for each of the aspects of the present disclosure, i.e., also belong to the disclosure.

BRIEF DESCRIPTION OF THE DRAWINGS

Further features, details, and advantages of the present disclosure emerge from the description given below of exemplary embodiments as well as on the basis of the drawings. In the figures:

FIG. 2 depicts an example of a schematic flowchart for a method for operating the medical system from FIG. 1.

DETAILED DESCRIPTION

Figure 1:
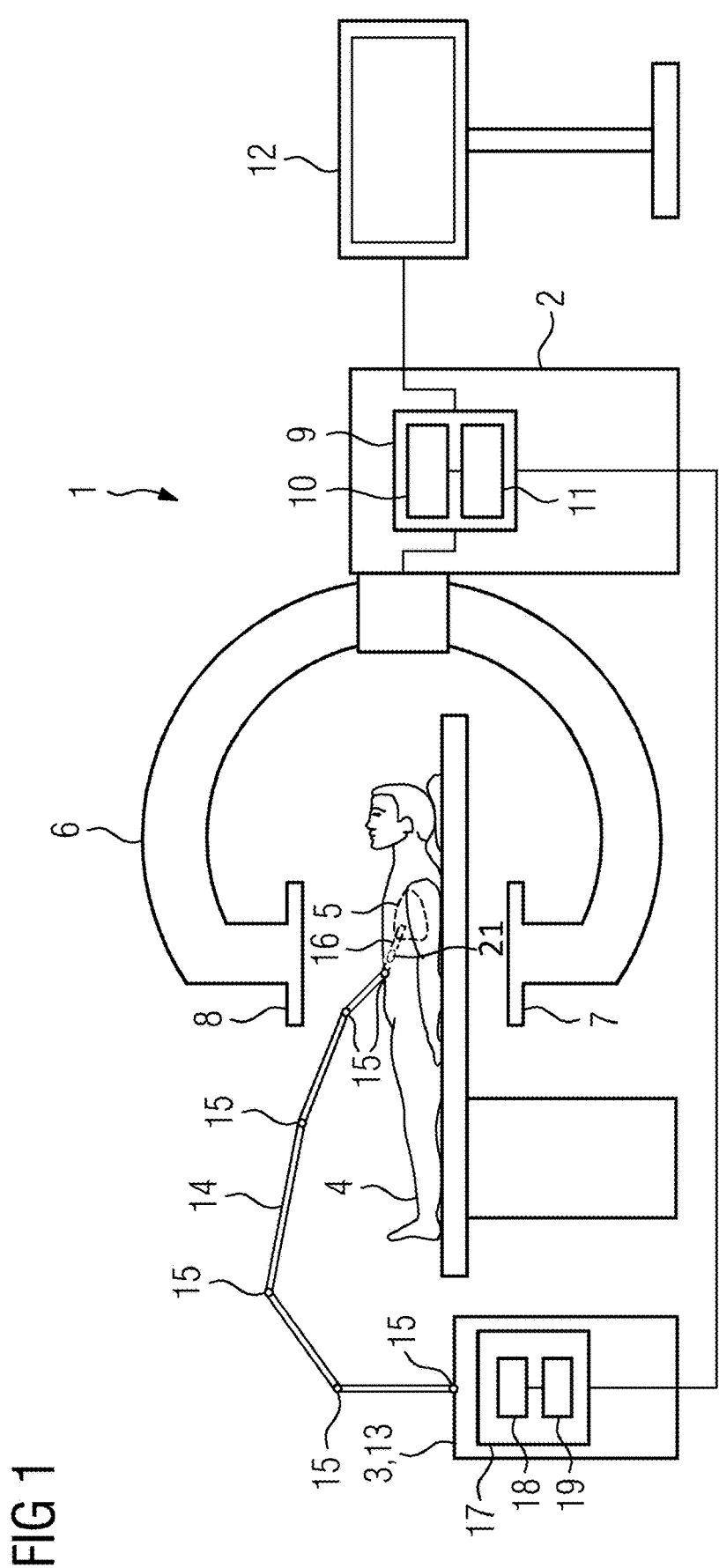
FIG. 1 depicts an example of a schematic diagram of a medical system with an imaging device and a robot.

In the exemplary embodiments, the described components of the forms of embodiment each represent individual features to be considered independently of one another, which also develop the disclosure independently of each other in each case and are thereby also to be seen individually or in a combination other than that shown as a component of the disclosure. Furthermore, the described forms of embodiment are also able to be supplemented by further of the features of the disclosure already described.

FIG. 1 depicts a schematic diagram of a medical system 1 with a medical imaging device, which is embodied here as an x-ray device 2, and a medical engineering robot 3. The system 1 serves, and is thus embodied and configured, to examine and, if necessary, treat examination objects. A patient 4 or an organ 5 of the patient 4 is shown in the present example as such an examination object.

To image or to examine the patient 4 or the organ 5, in the present example, the x-ray device 2 includes a C-arm 6 as well as a radiation source 7 held thereon and a detector 8 likewise held on the C-arm 6 opposite the radiation source 7. For processing of measurement data delivered by the detector 8, the x-ray device 2 further includes a data processing facility 9. This data processing facility 9 for its part includes a processor facility 10 as well as a computer-readable storage medium 11, to which the processor facility 10 is linked.

Also shown here is a display facility 12, which may be a screen or a Head-Mounted Display (HMD) or the like. Images of the respective examination object, thus here of the organ 5, for example, created by the data processing facility 9 may be shown by the display facility 12. To this end, the display facility 12 is connected in this figure to the x-ray device 2, in particular, to the data processing facility 9. The display facility 12 may be part of the system 1 or may merely be connected to the latter.

The robot 3 likewise connected to the x-ray device 2, in particular, to the data processing facility 9, here includes a robot foot 13, extending from which is a robot arm or instrument arm 14 of the robot 3. The instrument arm 14 is movable and to this end has a number of segments, which are coupled to one another by articulated joints 15 in each case. Arranged here on the end side, at an end of the instrument arm 14 facing away from the robot foot 13, is a medical instrument 16, which may be part of the robot 3 or may be held or guided by the robot 3. The instrument 16 may be a flexible catheter or a flexible endoscope or endoscopic instrument, for example.

In the present example, the robot 3 also has a control device 17 with a processor facility 18 and a computer-readable storage medium 19 connected thereto. The control device 17 is embodied here for control of the instrument arm 14, e.g., for controlling or setting a pose of the instrument arm 14. To this end, the robot 3 may have a drive able to be activated by the control device 17, which is not shown here for the sake of clarity and may be integrated into the articulated joints 15, for example.

Stored in the present example on one or both of the computer-readable storage media 11, 19 is a control or computer program for controlling or operating the system 1 or the respective components of the system 1, e.g., of the x-ray device 2 or of the robot 3, which is able to be executed in each case by the sensor facility 10 or by the processor facility 18.

FIG. 2 depicts an example of a schematic flowchart 20 for a method for operating the medical system 1. In this case, the flowchart 20 may represent the computer program or its functions, function blocks, or program modules. The flowchart 20 or the corresponding method or computer program will be explained below with reference to FIG. 1.

For examination and treatment of the patient 4, the instrument 16 may be guided to a specific target or Region of Interest (RoI). In such cases, it may be challenging or problematic if the patient 4 or the organ 5 moves, (e.g., as a result of the patient 4 breathing and as result of examination or treatment measures within the framework of the examination or of an intervention). This problem is counteracted by the system 1 or by the method described below.

In a method act S1 in the present example, a pre-interventional or pre-operative image dataset of the patient 4, in particular, of a part area of the patient 4 including the organ 5, is recorded, for example, by the x-ray device 1.

In a method act S2, on the basis of the pre-operative image dataset, a planning of the intervention is carried out, in particular, the target region and an instrument path, along which the instrument 16 is to be guided or navigated to the target region, are defined.

Moreover, in a method act S3, based on the pre-operative image dataset, a pre-operative pose or geometry of the patient 4, in particular, of the organ 5 and an environment of the planned instrument path, is established. The target region, the planned instrument path and the pre-operative pose or geometry will be predetermined as a reference or as target values to the system 1, in particular, to the robot 3 or to the control device 17.

In a method act S4, a registration is carried out between a coordinate system of the robot 3, a coordinate system of the x-ray device 2, and if necessary, the pre-operative image dataset. The coordinate system of the robot 3 is used in this case by the control device 17 for defining a current pose of the instrument arm 14. To determine this current pose, in the present example, the robot 3 has a position sensing system, which is integrated into the articulated joints 15, for example.

In a method act S5, the control device 17 simulates or predicts a behavior, on the basis of a predetermined biomechanical model of a part area of the patient 4 including at least the organ 5 and, for example, the environment of the planned instrument path, (e.g., a movement or deformation), of this part area under mechanical contact with the instrument arm 14 or the instrument 16, for example, during an insertion of the instrument 16 into the patient 4 and/or during a mechanical contact between the patient 4 and the instrument arm 14 as a result of the breathing or breathing movement of the patient 4.

In a method act S6, a supervision or tracking of the current pose or geometry of the patient 4 or of the part area takes place, for example, in parallel thereto, in particular during the intervention or examination. This may be done by live imaging, for example, a fluoroscopy imaging by the x-ray device 1, and/or by evaluation of measured values or sensor signals of a stress or load system integrated into the instrument arm 14. For example, mechanical contact between the instrument arm 14 and the patient 4 may be detected with this, a force occurring in such cases may be determined and, if necessary by parallel simulation on the basis of the biomechanical model, a change of shape, or deformation of the patient 4, for example, of the organ 5, may be determined.

The method acts S5 and S6 may thus be carried out in single or mutual dependency where necessary. Thus, a simulation might be carried out in each case on the basis of the biomechanical model, as soon as new data for current pose or geometry of the examination object is available in each case.

In a method act S7, the control device 17 compares the current pose or geometry of the patient 4 determined with the pre-operative pose or geometry predetermined, e.g., intended and established as reference, for example, likewise by the biomechanical model, a pose and/or force for the instrument arm 14, which is set, in order, by the instrument arm 14 through mechanical contact with the patient 4, to compensate for the difference possibly established, e.g., to set or to restore the pre-operative pose or geometry of the patient 4 predetermined as reference. In addition, or as an alternative, another pose or geometry, (e.g., for another part area such as the target region), may likewise be predetermined and compared with the current pose or geometry and treated as described, thus used as reference.

In a method act S8, the control device 17 activates the instrument arm 14 or the drive of the robot 3 in accordance with the determined pose and/or force needed and thereby causes the instrument arm 14 to come into mechanical contact in this way with the patient 4 and through this the respective predetermined pose for the patient 4 is reached or set. To this end, the patient 4 or a part area of the patient 4 may thus be actively moved and/or deformed, in particular, by the robot 3 or of the instrument arm 14, in order to make possible a carrying out of the examination or intervention that is simplified and is consistent with the preceding planning, for example.

The method acts described may each be repeated several times or continuously, in parallel to one another and/or carried out or run in an order other than the order shown and described schematically here.

It may be an objective here to reproduce the pre-operative pose or geometry of the patient 4 during the intervention. The pre-operative pose or geometry, which is mapped or shown by the pre-operative image dataset, is in this case in particular not influenced by the instrument arm 14 or the instrument 16. The pre-operative image dataset may be recorded in the absence of the instrument arm 14 and of the instrument 16. For determining the pose or geometry, for example, the pre-operative image dataset may be segmented with known methods, wherein this segmentation, or a model created therefrom, may then be provided, e.g., may be predetermined, as a reference, e.g., as the intended pose, to the control device 17.

The idea here is thus actively to position the robot 3 or the instrument arm 14, e.g., to set it or deform it, so that, through a displacement or deformation brought about through this of the patient 4 being in mechanical contact with the robot arm 14 in this case, the pose or geometry corresponding to the pre-operative image dataset or to the model created from it is retained or restored, is thus set, as reference during the intervention. To this end, the robot arm 14 may be actively controlled accordingly, in order to balance out or compensate for anatomical deformations during the intervention compared to a pre-operative state.

This may be carried out in each case during a specific breathing phase, for example, by the robot arm 14 being held during this breathing phase stiffened or in a set position at its respective position or in a position predetermined or determined automatically, e.g., using the drive if necessary. Likewise, this may be carried out while the patient 4 is breathing freely however, for example, by combination with data of a sensor 21 of the stress or load sensor system. When the stress or load sensor system is used to determine the respective pose, geometry, and deformation of the patient 4 as a result of the mechanical contact with the instrument arm 14, the use of the biomechanical model may advantageously be dispensed with if necessary, whereby the corresponding effort for providing the biomechanical model and executing the model may be avoided.

As discussed, the objective may likewise be not to set the pre-operative pose or geometry, but to set—ultimately any given—predetermined pose or geometry or deformation of the patient 4 by the robot 3. Within the framework of a bronchoscopy, for example, a specific geometry or a specific course of an airway or of breathing tubes may be desirable for more easily reaching a target region, (e.g., a lesion), and may be predetermined accordingly. Likewise, for example, the patient 4 or a part area of the patient 4 may be mechanically influenced, e.g., displaced or deformed, by the instrument arm 14, so that the respective target region is brought into a specific position or pose, in order to make it easier or make it possible to reach it. Thus, a pose of a lesion may be predetermined as the predetermined pose of at least a part of the patient 4, for example. The change of position of the lesion, (e.g., of the target region), as a result of the mechanical contact or a mechanical effect of the instrument arm 14 on the patient 4, may be modelled or predicted in advance in this case, (e.g., by or on the basis of the biomechanical model), by the control device 17 in each case, e.g., before a respective control or activation of the drive or of the instrument arm 14. A further application case is, for example, the setting of a predetermined pose or deformation of a part of the patient 4 in order, for example, to reach or to set a more favorable, for example, easier-to-reach, exit for the instrument 16 from the bronchi of the patient 4.

By appropriate modelling, it may be simulated or predicted in such cases how the patient 4 or a part of the patient 4, for example, the respective target region or a vessel along the instrument path or the like, will move or behave as a function of a given movement or pose of the robot arm 14. This in its turn makes it possible to control the robot arm 14 automatically accordingly, in order to cause specific forces, movements, or deformations in the patient 4, in order to set the respective predetermined, e.g., desired or intended, pose.

Overall the described examples show how an active robot control may be realized and used for an anatomical deformation, in order to make possible a reliable navigation of instruments or devices in a low-stress way for a respective examination object.

Although the disclosure has been illustrated and described in detail using the exemplary embodiments, the disclosure is not limited by the disclosed examples, and a person skilled in the art may derive other variations therefrom without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A medical engineering robot comprising:
   a movable instrument arm,
   a drive configured to move the instrument arm; and
   a controller connected to the drive for automatic control of a pose of the instrument arm,
   wherein the controller is configured, by controlling the pose of the instrument arm relative to a respective examination object to be treated or to be examined by the medical engineering robot, to bring the instrument arm automatically into contact with the examination object and to set a predetermined pose of the examination object,
   wherein the predetermined pose of the examination object is configured to be detected by a medical imaging device,
   wherein a corresponding pre-interventional image data set depicting the predetermined pose of the examination object is configured to be recorded by the medical imaging device in an absence of the instrument arm, and
   wherein the controller is configured to compare a current pose of the examination object under examination with the predetermined pose of the examination object and to compensate for any difference between the current pose and the predetermined pose by controlling the instrument arm in mechanical contact with the examination object.

2. The medical engineering robot of claim 1, wherein the medical engineering robot is configured, by active control of the instrument arm relative to the examination object, to counteract a deformation of the examination object.

3. The medical engineering robot of claim 1, wherein the medical engineering robot is configured to assess an ability for an instrument to reach a predetermined target region based on at least one predetermined geometrical criterion and to control the instrument arm in relation to the examination object as a function of the ability for the instrument to reach the predetermined target region, in order to improve the ability for the instrument to reach the predetermined target region.

4. The medical engineering robot of claim 1, further comprising:
a medical instrument,
wherein the instrument arm is configured as the medical instrument or the medical instrument is fastened to the instrument arm.

5. The medical engineering robot of claim 4, wherein the medical instrument is a catheter, an endoscope, or a combination thereof.

6. The medical engineering robot of claim 4, wherein at least a part of the medical instrument is configured to be visible to x-rays.

7. The medical engineering robot of claim 1, wherein the medical engineering robot is configured to acquire breathing data that specifies a respective current breathing phase of the examination object, and
wherein the controller is configured to control the pose of the instrument arm as a function of the breathing data.

8. The medical engineering robot of claim 1, wherein the controller contains a predetermined biomechanical model of at least a part of the examination object and is configured, by simulating a behavior of at least the part of the examination object under mechanical contact with the instrument arm, to automatically determine by the predetermined biomechanical model the pose of the instrument arm and/or a force to be exerted by the instrument arm on the examination object to set the predetermined pose of the examination object and to create corresponding control signals for the drive.

9. The medical engineering robot of claim 1, further comprising:
a sensor arranged on the instrument arm for determining a mechanical property of a part of the examination object in mechanical contact with the instrument arm,
wherein the controller is configured to automatically determine the pose of the instrument arm and/or a force to be exerted by the instrument arm on the examination object for setting the predetermined pose of the examination object as a function of the mechanical property determined.

10. The medical engineering robot of claim 9, wherein the sensor comprises a force sensor, a moment sensor, a bending sensor, an acceleration sensor, an angle sensor, an inertial measurement unit sensor, a fiber Bragg grating sensor, or a combination thereof.

11. The medical engineering robot of claim 10, wherein the medical imaging device is an X-ray imaging device.

12. The medical engineering robot of claim 1, wherein the medical imaging device is an X-ray imaging device.

13. A medical engineering robot comprising:
a movable instrument arm,
a drive configured to move the instrument arm; and
a controller connected to the drive for automatic control of a pose of the instrument arm,
wherein the controller is configured, by controlling the pose of the instrument arm relative to a respective examination object to be treated or to be examined by the medical engineering robot, to bring the instrument arm automatically into contact with the examination object and to set a predetermined pose of the examination object,
wherein the medical engineering robot is configured to acquire breathing data that specifies a respective current breathing phase of the examination object,
wherein the controller is configured to control the pose of the instrument arm as a function of the breathing data, and
wherein the controller is configured, in a predetermined breathing phase in each case, in which the examination object comes into contact with the instrument arm because of a breathing movement of the examination object, to stiffen the instrument arm in a predetermined position and thereby to limit the breathing movement of the examination object.

14. A medical system comprising:
a medical imaging device configured to image an examination object; and
a medical engineering robot connected to the medical imaging device, the medical engineering robot comprising:
a movable instrument arm,
a drive configured to move the instrument arm; and
a controller connected to the drive for automatic control of a pose of the instrument arm,
wherein the controller of the medical engineering robot is configured to automatically control the pose of the instrument arm of the medical engineering robot as a function of data provided by the medical imaging device and to automatically set a predetermined pose of the examination object and bring the instrument arm into contact with the examination object,
wherein the predetermined pose of the examination object is configured to be detected by the medical imaging device,
wherein a corresponding pre-interventional image data set depicting the predetermined pose of the examination object is configured to be recorded by the medical imaging device in an absence of the instrument arm, and
wherein the controller is configured to compare a current pose of the examination object under examination with the predetermined pose of the examination object and to compensate for any difference between the current pose and the predetermined pose by controlling the instrument arm in mechanical contact with the examination object.

15. The medical system of claim 14, wherein the medical imaging device is an X-ray imaging device.

16. A method for operating a medical engineering robot or a medical system, the method comprising:
determining an intended pose of at least a part of a respective examination object;
automatically determining a pose of an instrument arm or the medical engineering robot or the medical system relative to the examination object and/or a force to be exerted by the instrument arm on the examination object for setting the intended pose of the examination object;
automatically setting, by a controller of the instrument arm in accordance with the determined pose and/or the force to be exerted, the intended pose of the examination object; and
bringing, by the controller, the instrument arm automatically into contact with the examination object by controlling the pose of the instrument arm relative to the examination object,
wherein the intended pose of the examination object is detected by a medical imaging device,
wherein a corresponding pre-interventional image data set depicting the intended pose of the examination object is recorded by the medical imaging device in an absence of the instrument arm, and
wherein the controller compares a current pose of the examination object under examination with the intended pose of the examination object and compensates for any difference between the current pose and the intended pose by controlling the instrument arm in mechanical contact with the examination object.

17. The method of claim 16, further comprising:
determining a pre-interventional pose of the examination object in accordance with an image dataset created pre-interventionally for intervention planning of the examination object,
wherein the pre-interventional pose is determined as the intended pose of the examination object.

18. The method of claim 16, wherein the medical imaging device is an X-ray imaging device.

19. A non-transitory computer-readable storage medium having a computer program stored thereon, wherein the computer program, when executed by a computer of a medical engineering robot or a medical system, to cause the medical engineering robot or the medical system to:
determine an intended pose of at least a part of a respective examination object;
automatically determine a pose of an instrument arm or the medical engineering robot or the medical system relative to the examination object and/or a force to be exerted by the instrument arm on the examination object for setting the intended pose of the examination object;
automatically set the intended pose of the examination object in accordance with the determined pose and/or the force to be exerted; and
bring the instrument arm automatically into contact with the examination object by controlling the pose of the instrument arm relative to the examination object,
wherein the intended pose of the examination object is configured to be detected by a medical imaging device,
wherein a corresponding pre-interventional image data set depicting the intended pose of the examination object is configured to be recorded by the medical imaging device in an absence of the instrument arm, and
wherein the medical engineering robot is configured to compare a current pose of the examination object under examination with the intended pose of the examination object and to compensate for any difference between the current pose and the intended pose by controlling the instrument arm in mechanical contact with the examination object.

20. The non-transitory computer-readable storage medium of claim 19, wherein the medical imaging device is an X-ray imaging device.

* * * * *